United States Patent [19]

Geelhoed

[11] Patent Number: 5,702,117
[45] Date of Patent: Dec. 30, 1997

[54] TROLLEY INTENDED FOR A MEDICAL APPARATUS AND COMPRISING WHEELS PROVIDED WITH A CABLE PUSHER

[75] Inventor: Frans E. N. Geelhoed, Eindhoven, Netherlands

[73] Assignee: U.S. Philips Corporation, New York, N.Y.

[21] Appl. No.: 572,218

[22] Filed: Dec. 13, 1995

[30] Foreign Application Priority Data

Dec. 19, 1994 [EP] European Pat. Off. .............. 94203668

[51] Int. Cl.$^6$ ...................................................... B60R 19/54
[52] U.S. Cl. ............................................. 280/160; 16/18 CG
[58] Field of Search .............................. 280/160, 160.1, 280/5.2, 5.32; 16/18 CG, 18 B

[56] References Cited

U.S. PATENT DOCUMENTS

| | | | |
|---|---|---|---|
| 2,450,062 | 9/1948 | Voss et al. | 280/160 X |
| 2,533,403 | 12/1950 | Schultz | 16/18 CG |
| 3,719,370 | 3/1973 | Gintick et al. | 16/18 CG X |
| 4,025,099 | 5/1977 | Virden | 280/160 X |
| 4,887,287 | 12/1989 | Cobben | 378/198 |
| 4,977,588 | 12/1990 | Van Der Ende | 378/196 |
| 5,170,528 | 12/1992 | Navar et al. | 280/160 X |
| 5,339,350 | 8/1994 | Thelosen | 378/198 |

FOREIGN PATENT DOCUMENTS

| | | | |
|---|---|---|---|
| 85984 | 8/1983 | European Pat. Off. | 16/18 CG |
| 223517 | 4/1943 | Switzerland | 16/18 B |

*Primary Examiner*—Kevin Hurley
*Attorney, Agent, or Firm*—Jack D. Slobod

[57] ABSTRACT

A trolley intended for a medical apparatus and comprising wheels for displacement on a floor surface. In order to push aside cables running on the floor of the working environment, the wheels are provided with a cable pusher having a pushing edge. The plate constituting the cable pusher is provided with approximately triangular cut-outs which receive stationary cams. If no external forces act on the plate, it is pressed onto the cams by springs in such a manner that the apex of the triangular cut-outs bears on the cams. The springs are proportioned so that an obstructing cable is pushed aside by the plate; however, when this plate comes into contact with a fixed obstacle, for example a threshold, the plate is pushed upwards. Damaging of the cable pusher is thus avoided and the risk of overturning of the trolley is reduced.

5 Claims, 3 Drawing Sheets

TROLLEY INTENDED FOR A MEDICAL APPARATUS AND COMPRISING WHEELS PROVIDED WITH A CABLE PUSHER

BACKGROUND OF THE INVENTION

1. Field of the Invention

The invention relates to a trolley intended for a medical apparatus and comprising a base provided with wheels enabling displacement of the trolley on a floor surface, at least one of the wheels being provided with a cable pusher having a pushing edge situated a predetermined distance above the floor surface.

2. Description of the Related Art

A trolley of this kind is known from European Patent Application EP 0 601 636 laid open to public inspection. The advantage of a mobile trolley consists in that it can be readily moved to any desired position relative to a patient, for example in a bed or on a stationary patient table. Generally speaking, the apparatus is connected to a power supply source and to auxiliary equipment, such as equipment for the storage and processing of information, via a number of electric cables. An advantage of a trolley comprising wheels provided with a cable pusher consists in that during displacement of the apparatus the operator need not continuously remove cables running in front of the wheels because, thanks to the cable pusher, the wheels cannot be blocked by the cables on the floor.

The known trolley comprises a cable pusher which consists of an approximately horizontally arranged ring which is made of a rigid material and which encloses the wheel a given distance above the floor surface. Because, generally speaking, it will be necessary to displace the trolley over rather large distances from time to time, for example to another room, in such cases the trolley will often have to cross thresholds and be moved into and out of elevators. The rings occupying a low position may then constitute an obstruction. Therefore, the rings are connected to the base so as to be displaceable in the vertical direction, connection being realised in such a manner that the rings have two stable positions above the floor surface. During normal operation of the apparatus, the rings can then be adjusted to a first position and during transport they can be adjusted to a second (higher) position. Because the rings must be displaced by hand, the operator can easily forget to move the ring-shaped cable pusher upwards while crossing a fixed obstacle such as a threshold. Consequently, the cable pusher or the wheel suspension could be damaged. Moreover, nowadays authorities tend to impose increasingly severe requirements as regards the stability of trolleys in working environments such as hospitals. For example, there is the requirement that when an unattended trolley travelling at a given speed collides with an obstacle (for example, a threshold) of a given height, it may not be overturned by such a collision. (For example, see "International Standard" IEC 601-62B CA 108A). A fixed ring of a rigid material will then increase the tendency of overturning rather than reduce it, because the ring will become stuck in front of the threshold so that the wheel cannot cross the threshold.

SUMMARY OF THE INVENTION

It is an object of the invention to provide a trolley of the kind set forth such that cables running on the floor can be kept away from the wheels, without intervention by the attendants, and threshold-like obstacles can be passed without further intervention by the attendants. To this end, the X-ray apparatus in accordance with the invention is characterized in that the cable pusher comprises a surface (the cut-out surface) which extends perpendicularly to the shaft of the associated wheel and a boundary of which constitutes the pushing edge, in said cut-out surface there being provided cut-outs which receive a respective cam which is rigidly arranged relative to the wheel shaft, said cams being offset relative to one another, parallel to the floor surface, each of said cut-outs comprising two boundaries which extend towards the floor surface and which meet at the area of an equilibrium suspension point, there being provided resilient means which press the cut-out surface with the cams in the equilibrium suspension points.

The cut-out surface extending perpendicularly to the shaft of the associated wheel is formed physically, for example by a flat plate or by a flat wire frame. Any cables which are in the way are pushed aside by the lower side of the plate or the wire frame because the resilient means pressing the cut-out surface with the cams in the equilibrium suspension points are proportioned so that the plate does not yield to the (comparatively low resistance) of a cable. The lower side of the plate thus constitutes the pushing edge. From each of the cut-outs successively formed in the plate there projects a cam on which, in the absence of collision forces, the plate bears by resilience by way of its equilibrium suspension points. Should the cable collide with a fixed obstacle, the force acting on the plate will be much greater than the resistance of a cable. The resilient means then enable the plate to be shifted relative to the cams; the plate will thus be shifted upwards against the spring force, so that the cable pusher yields to the threshold and damage is prevented.

In an embodiment which can be simply and readily manufactured, the cable pusher in accordance with the invention is constructed so as to have a cut-out surface which is formed by a flat plate comprising mainly triangular cut-outs. The downwards facing sides of the triangles then constitute the boundaries extending towards the floor surface.

In another embodiment the cable pusher in accordance with the invention is constructed so as to comprise cams which are shaped as a cylinder and equilibrium suspension points which are shaped as an arc of circle of the same radius as the cylinder. When the cut-out surface has been pushed up after having been in contact with a fixed obstacle, it can then readily return to its equilibrium position guided by the downwards oriented sides of the triangles and the circular shape enclosed thereby. The return to the equilibrium position is further facilitated in that the boundaries meeting at the area of an equilibrium suspension point enclose an angle of at least 60°. As a result of this choice of this angle, it is avoided that the cable pusher does not suitably return to its equilibrium position due to friction between the cut-out surface and the cams.

Returning to the equilibrium position is further stimulated in that the resilient means are formed by two spring elements whose respective spring forces act in a direction from the respective cut-outs towards a point on the floor surface between the two cut-outs.

These and other aspects of the invention will be apparent from and elucidated with reference to the embodiments described hereinafter.

DETAILED DESCRIPTION OF THE PREFERRED EMBODIMENTS

Figure 1:
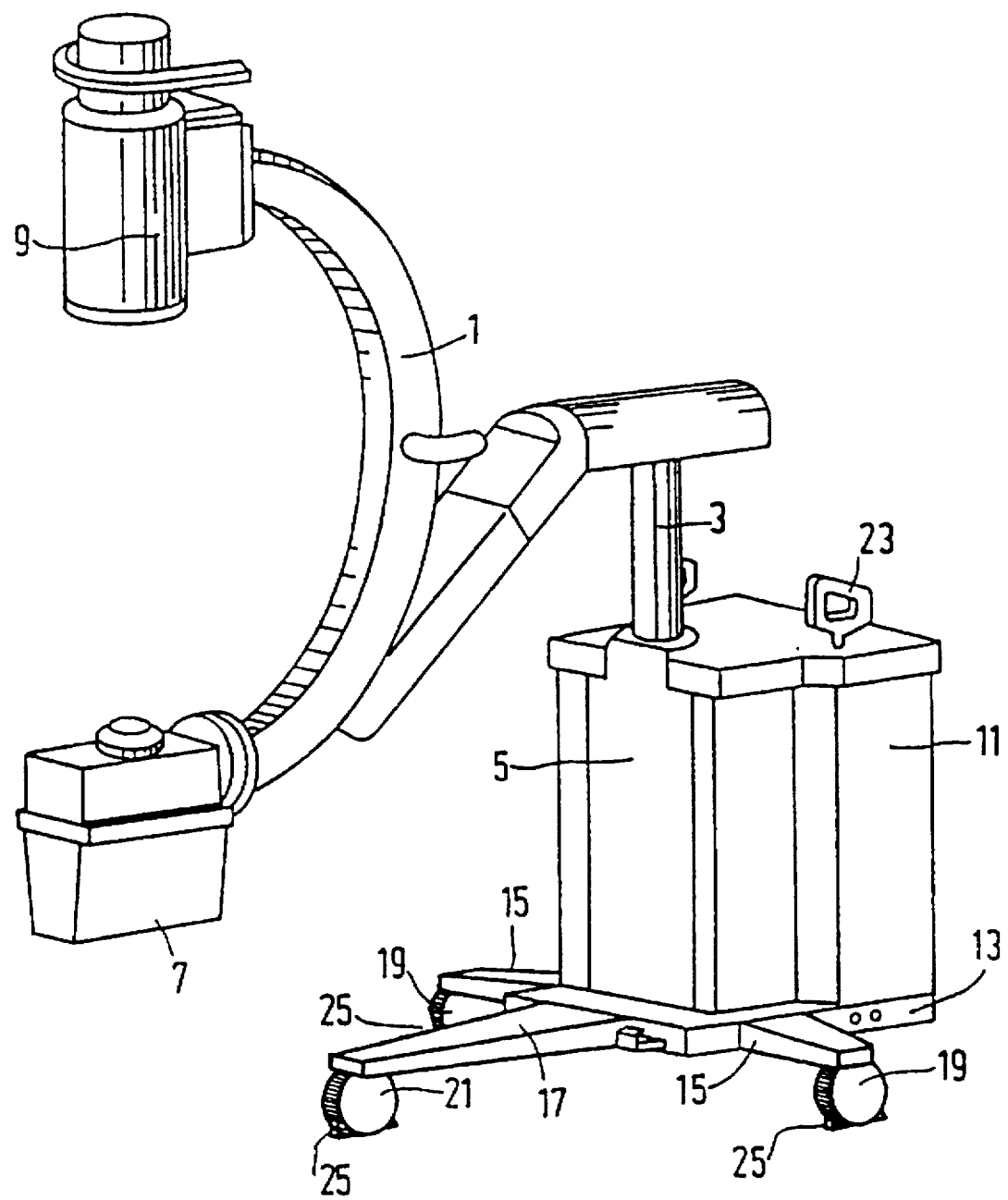
FIG. 1 is a simplified representation of an embodiment of a trolley in the form of an X-ray apparatus in accordance with the invention.

FIG. 1 shows a trolley in the form of a mobile X-ray apparatus which comprises a frame which consists of a C-arc 1 in the present embodiment; this arc is secured to a cylindrical rod 3 which is mounted in a columnar section 5 in such a manner that its height is adjustable. An X-ray source 7 and an X-ray detector 9 are mounted opposite one another at the free ends of the C-arc. The columnar section 5 and an electric module 11 are arranged on a mobile base 13 which comprises two laterally projecting arms 15 and a forwards projecting arm 17. Near the end of each lateral arm 15 there is mounted a respective wheel 19 and a wheel 21 is mounted near the end of the front arm 17. The wheels 19 can be controlled, for example by means of a control handle 23 whereas the front wheel 21 may be a swivel wheel. Thanks to the wheels 19, 21, the apparatus can be readily displaced on an approximately horizontal floor surface which is not shown in FIG. 1. The wheels 19, 21 could be blocked by cables which run on the floor surface (not shown), for example in order to connect the electric module 11 to the electric mains and to image and data processing auxiliary equipment. In order to prevent such blocking, each of the wheels 19, 21 is provided with a cable pusher 25 which is situated a small distance above the floor surface. This distance is less than the thickness of the cables associated with the apparatus. A distance of at least one millimeter above the floor surface is desirable so as to prevent contact between the cable pushers 25 and small irregularities in the floor surface, such as seams in the floor coverings. It has been found in practice that a distance of approximately 3 mm is satisfactory. The cable pushers 25 are made of a rigid material (for example, a hard synthetic material) in order to prevent deformation when they contact the cables, since otherwise the cable could become stuck underneath the ring.

Figure 2:
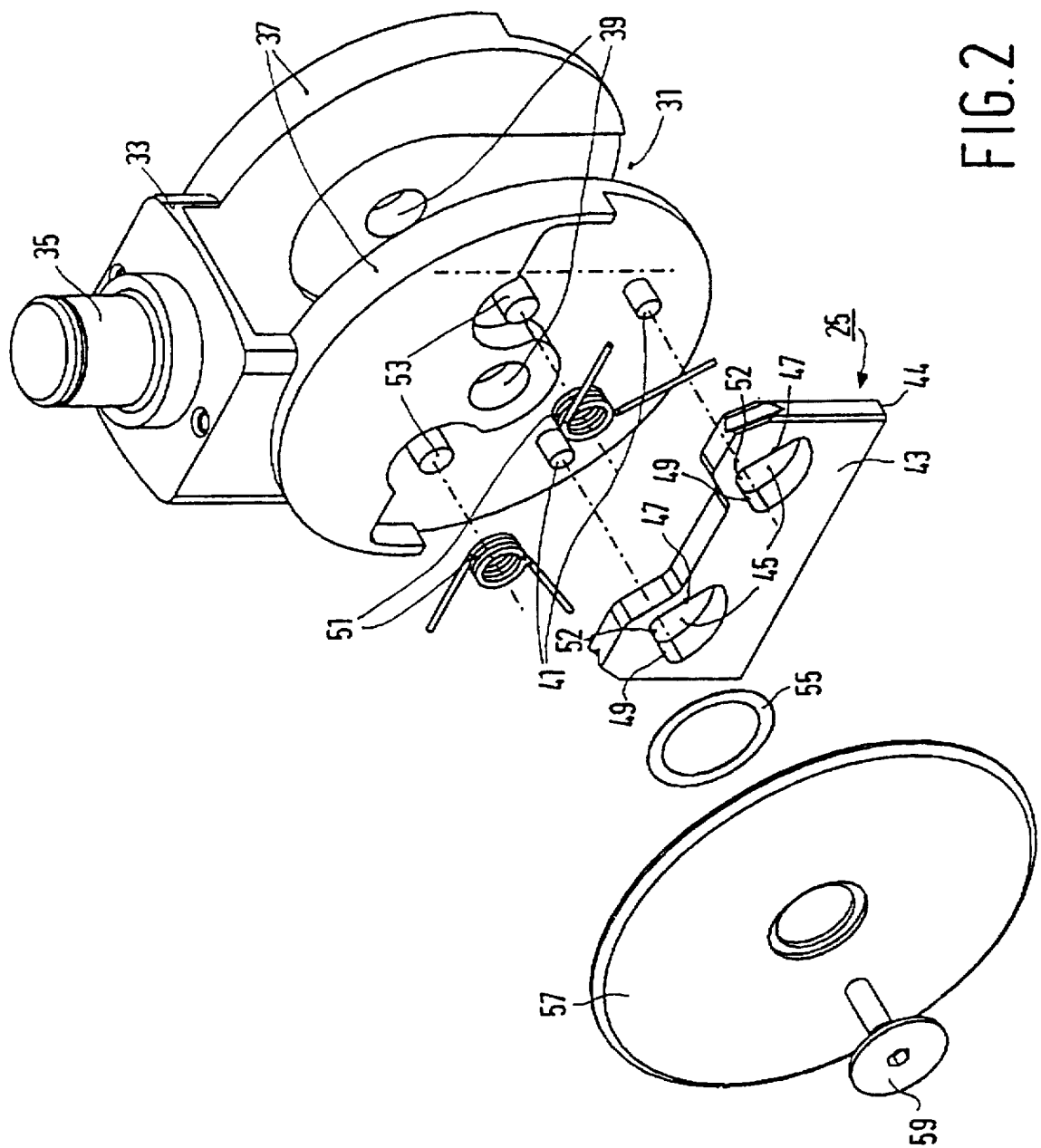
FIG. 2 is an exploded view of a wheel holder with a cable pusher in accordance with the invention.

FIG. 2 is an exploded view of a wheel holder with a cable pusher. Because this wheel holder is intended for use as a swivel wheel, the wheel holder comprises a vertical shaft 35 which is mounted on the holder housing 33 and around which the wheel can freely rotate. The holder housing 33 is integral with two mounting plates 37 in openings 39 of which the shaft of the wheel 31 (not shown) can be journalled, said plates also serving as supports for the various mounting elements for the cable pusher. Each of the mounting plates 37 also comprises two cams 41 which are arranged so as to be offset relative to one another, parallel to the floor surface. On the mounting plate there is provided a plate 43 which defines a surface (referred to hereinafter as the cut-out surface), a boundary of which (i.e. the lower edge 44) constitutes the pushing edge for pushing aside the cables. The cut-out surface is referred to as such because two cut-outs 45 are provided therein. Each of these cut-outs 45 comprises two boundaries 47 and 49 extending rewards the floor surface. The boundaries 47 and 49 meet at the area of the apex 52 of the triangular cut-outs. Because the plate 43 is suspended in these points 52 in the state of equilibrium, these points are referred to as the equilibrium suspension points. In the rest state, the plate 43 is pressed with its equilibrium suspension points 52 against the cams 41, projecting into the cut-outs 45, by the springs 51 which are provided on spring studs 53. The various parts to be mounted on the mounting plate 37 are located on this plate by a cover plate 57 which is provided on the mounting plate 37 with an intermediate washer 55. The cover plate 57 is secured by means of a screw 59.

Figure 3A:
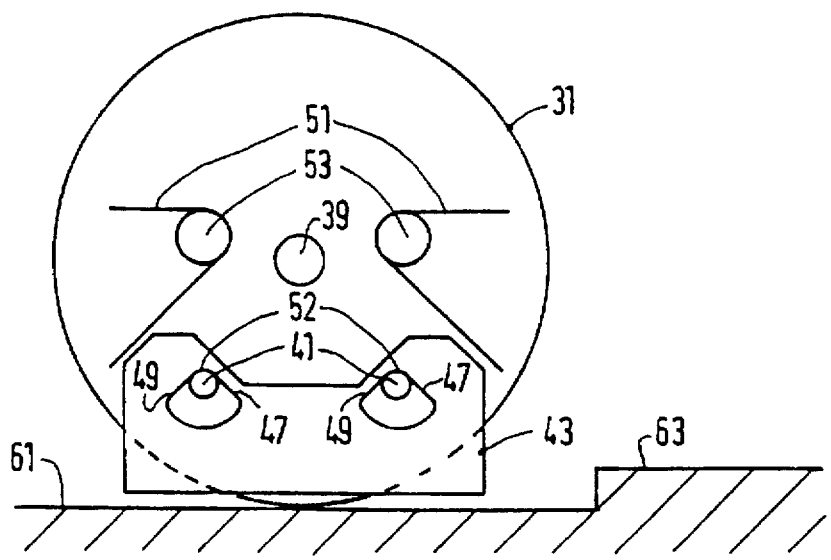
FIG. 3a is a side elevation of a wheel with a cable pusher which is not in contact with an obstacle.
Figure 3B:
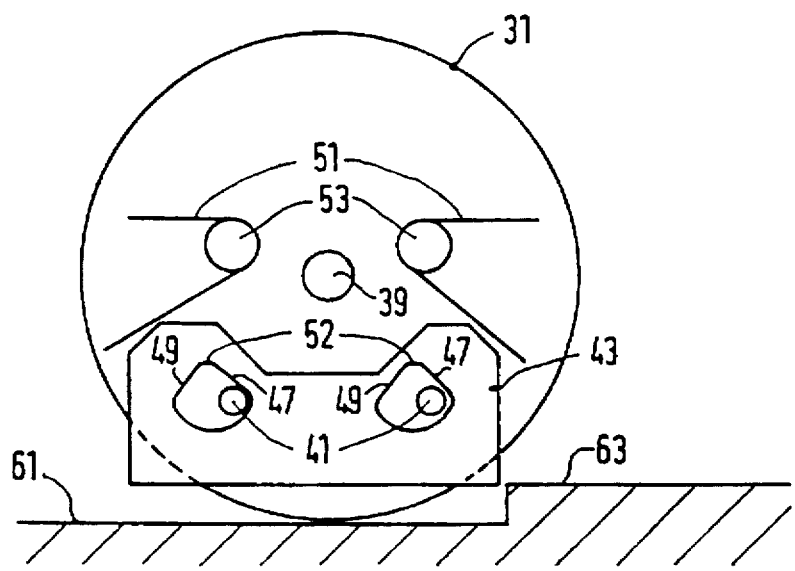
FIG. 3b is a side elevation of a wheel with a cable pusher which has been pushed up by an obstacle.

FIGS. 3a and 3b are simplified side elevations of a wheel with a cable pusher, the cover plate 57 having been omitted for the sake of clarity. In FIG. 3a the plate 43 is not in contact with an obstacle, but in FIG. 3b it is. In FIG. 3a the springs 51 press the plate 43 against the cams 41 by way of its equilibrium suspension points 52. The force of the springs 51 is chosen in such a manner that a loose cable on the floor 61 in front of the wheel can be pushed aside by the plate 43, without the plate being pressed out of its state of equilibrium. However, if this plate 43 collides with a fixed obstacle 63, the plate is pushed back. Possibly after having been slightly tilted upwards at the rear, the plate 43 then assumes the position shown in FIG. 3b. The wheel can then pass the threshold 63, after which the plate 43 is pushed back to its equilibrium position again by the springs.

I claim:

1. A trolley intended for a medical apparatus and comprising a base provided with wheels enabling displacement of the trolley on a floor surface, at least one of the wheels being provided with a cable pusher having a pushing edge situated a predetermined distance above the floor surface, characterized in that:
    a) the cable pusher comprises a cut-out surface which extends perpendicularly to the shaft of the associated wheel and a boundary of which constitutes the pushing
    b) in said cut-out surface there are provided cut-outs which receive a respective cam which is rigidly arranged relative to the wheel shaft, said cams being offset relative to one another, parallel to the floor surface,
    c) each of said cut-outs comprises two boundaries which extend towards the floor surface,
    d) the boundaries meet at the area of an equilibrium suspension point,
    e) and resilient means are provided which press the cut-out surface with the cams in the equilibrium suspension points.

2. A trolley as claimed in claim 1, characterized in that the cut-out surface is formed by a flat plate comprising mainly triangular cut-outs.

3. A trolley as claimed in claim 1, characterized in that the cams are shaped as a cylinder and the equilibrium suspension points are shaped as an arc of circle of the same radius as the cylinder.

4. A trolley as claimed in claim 1, characterized in that the boundaries which meet at the area of an equilibrium suspension point enclose an angle of at least 60°.

5. A trolley as claimed in claim 1, characterized in that the resilient means are formed by two spring elements whose respective spring forces act in a direction from the respective cut-outs towards a point on the floor surface between the two cut-outs.

* * * * *